United States Patent [19]

Lyons

[11] Patent Number: 5,616,342
[45] Date of Patent: Apr. 1, 1997

[54] EMULSIOIN SUITABLE FOR ADMINISTERING A POORLY WATER-SOLUBLE PHOTOSENSITIZING COMPOUND AND USE THEREOF

[75] Inventor: Robert T. Lyons, Cary, N.C.

[73] Assignees: PDT, Inc., Santa Barbara, Calif.; Pharmacia & Upjohn AB, Stockholm, Sweden

[21] Appl. No.: 419,911

[22] Filed: Apr. 11, 1995

[51] Int. Cl.$^6$ .......................... A61K 9/127; A61K 31/40
[52] U.S. Cl. .............................. 424/450; 514/450
[58] Field of Search .................. 424/450; 514/410

[56] References Cited

U.S. PATENT DOCUMENTS

| | | | |
|---|---|---|---|
| Re. 32,393 | 4/1987 | Wretlind et al. | 514/219 |
| 4,115,313 | 9/1978 | Lyon et al. | 252/309 |
| 4,280,996 | 7/1981 | Okamoto et al. | 424/199 |
| 4,703,062 | 10/1987 | Blackburn et al. | 514/552 |
| 4,711,902 | 12/1987 | Serno | 514/356 |
| 4,784,845 | 11/1988 | Desai et al. | 424/80 |
| 4,877,872 | 10/1989 | Morgan et al. | 540/145 |
| 4,914,088 | 4/1990 | Glonek et al. | 514/76 |
| 4,988,808 | 1/1991 | Morgan et al. | 540/145 |
| 5,109,129 | 4/1992 | Morgan et al. | 540/145 |
| 5,179,120 | 1/1993 | Vogel et al. | 514/410 |
| 5,244,671 | 9/1993 | Vogel et al. | 424/450 |
| 5,250,668 | 10/1993 | Morgan et al. | 540/145 |
| 5,286,474 | 2/1994 | Gust, Jr. et al. | 424/7.1 |
| 5,364,632 | 11/1994 | Benita et al. | 424/450 |

FOREIGN PATENT DOCUMENTS

| | | |
|---|---|---|
| 0361928A2 | 4/1980 | European Pat. Off. . |
| 0253472A1 | 1/1987 | European Pat. Off. . |
| 0215313A2 | 3/1987 | European Pat. Off. . |
| 0214501A2 | 3/1987 | European Pat. Off. . |
| 0391369A2 | 10/1990 | European Pat. Off. . |
| 0399843A2 | 11/1990 | European Pat. Off. . |
| 0480690A1 | 4/1991 | European Pat. Off. . |
| 0459148A2 | 12/1991 | European Pat. Off. . |
| 0391369B1 | 8/1994 | European Pat. Off. . |
| WO89/01327 | 2/1989 | WIPO . |

OTHER PUBLICATIONS

Richter et al., Liposomal Delivery of a Photosensitizer, Benzoporphyrin Derivative Monoacid Ring A (BPD), to Tumor Tissue in a Mouse Tumor Model, Photochemistry and Photobiology, vol. 57, No. 6, (1993), pp. 1000–1006.

Cannon, Journal of Pharmaceutical Sciences, Pharmaceutics and Drug Delivery Aspects of Heme and Porphyrin Therapy, Journal of Pharmaceutical Sciences, vol. 83, No. 5 (1993), pp. 435–446.

Benita et al., Physostigmine emulsion: a new injectable controlled release delivery system, International Journal of Pharmaceutics, vol. 30, (1986), pp. 47–55.

Schuberth et al., Intravenous Infusion of Fat Emulsions, Phosphatides and Emulsifying Agents, ACTA Chirurgica Scandinavica Supplementum 278, pp. 3–21.

*Primary Examiner*—Carlos Azpuru
*Attorney, Agent, or Firm*—Pollock, Vande Sande & Priddy

[57] ABSTRACT

Emulsion comprising a lipoid as a hydrophobic phase dispersed in a hydrophilic phase, a poorly water-soluble photosensitizing compound, surfactant, and as a cosurfactant a salt of a bile acid is provided that is suitable for administering to a patient.

31 Claims, 1 Drawing Sheet

EMULSIOIN SUITABLE FOR ADMINISTERING A POORLY WATER-SOLUBLE PHOTOSENSITIZING COMPOUND AND USE THEREOF

TECHNICAL FIELD

The present invention is concerned with providing emulsions of poorly water-soluble, pharmacologically active, photosensitizing compounds, and especially of pyrrole-based macrocyclic compounds. Such compounds include naturally occurring or synthetic porphyrins, naturally occurring or synthetic chlorins, naturally occurring or synthetic bacteriochlorins, synthetic isobacteriochlorins, phthalocyanines, naphthalocyanines, and expanded pyrrole-based macrocyclic systems such as porphycenes, sapphyrins, and texaphyrins, and derivatives thereof. Emulsions of the present invention are useful in oxygen-dependent and oxygen-independent phototherapy and/or photodiagnosis. Emulsions of the present invention are capable of intravenous administration.

BACKGROUND OF THE INVENTION

Photoreactive drugs are unique compounds which are inactive until exposed to light of a specific wavelength. Photodynamic therapy begins with the intravenous administration of a selected photoreactive drug to a patient. At first, the drug disperses throughout the body and is taken up by most cells, whether normal or not. After a period of time usually between 3 and 48 hours, the drug clears from most normal tissue and is retained to a greater degree by hyperproliferating or otherwise abnormal cells.

Photodynamic activity begins when the photosensitizer is exposed to light of a specific wavelength. This light, usually but not necessarily generated by a laser and transmitted through a specially designed fiber optic, activates the intracellular drug. Activation results in the formation of cytotoxic species (free radicals and/or singlet oxygen) which rapidly and selectively destroy the cells in which the photosensitizer is located. Certain wavelengths of light are optimal for therapeutic destruction of rapidly proliferating cells, while other wavelengths induce a visible fluorescence and are therefore ideal for diagnostic identification of these cells.

A new generation of photosensitizers is currently under investigation or development for use in photodynamic therapy. These include chlorins (such as benzoporphyrin derivatives), purpurins, and phthalocyanines, all of which have strong hydrophobic characteristics. Extensive animal studies have shown that such poorly water-soluble pyrrole-derived macrocycles tend to maximize both diagnostic and therapeutic specificity by virtue of a high retention differential between abnormal and normal cells. While the water solubility of porphyrins can be enhanced by suitable derivatization, a significant loss of tissue specificity may occur. Therefore, simple aqueous/alcohol solutions of relatively water-soluble pyrrole-based macrocycles have proven to be much less useful.

These new generation photosensitizers often pose serious challenges to achieving suitable formulation. For more lipophilic porphyrins, dimethylsulfoxide (DMSO)/water solutions are suitable for preliminary studies either in vitro or in vivo. However, for clinical applications, dimethylsulfoxide is not considered to be an appropriate vehicle. Micellar preparations of poorly water-soluble porphyrin derivatives may be made, using the non-ionic surfactant Cremophor EL (polyoxyethylated castor oil), but serious anaphalactoid reactions have been reported and premedication with steroids may be required. Various organic solvent mixtures (e.g. polyethylene glycol, propylene glycol, t-butanol, dimethylacetamide) will also solubilize certain lipophilic porphyrin derivatives. However, such systems are often associated with pain on injection and phlebitis, due in part to local vein irritation by the solvent and to drug precipitation upon dilution in the bloodstream. In addition, these solvents are poorly metabolizable and are associated with other undesirable toxic side effects.

In addition to hydrophobic character, these new generation porphyrins often exhibit a high tendency to form aggregates due to "sandwich style" interactions between their planar rings. Molecular aggregates hinder solubilization of crystalline drug and complicate efforts to produce particle-free formulations with adequate storage stability.

Yet another formulation difficulty is the well-documented sensitivity of many pyrrole-based macrocycles to photooxidation.

Several liposomal porphyrin formulations are in human clinical trials. These include benzoporphyrin derivative (Quadra Logic Technologies, Inc., Vancouver, B.C., Canada) and Zn-phthalocyanine (CIBA-GEIGY Ltd., Basel, Switzerland). Liposomes are submicron, hollow vesicles consisting of hydrated, synthetic phospholipids arranged in a bilayer structure. However, to the best of applicant's knowledge, there are no heat-stable oil-in-water emulsions available that are suitable for injecting poorly water-soluble photosensitizing drugs. An oil-in-water emulsion is a microscopic dispersion of oil droplets in a continuous aqueous phase with a surfactant used to stabilize the dispersed droplets.

SUMMARY OF THE INVENTION

The present invention is concerned with an emulsion suitable for administering a poorly water-soluble, pharmacologically active, photosensitizing compound to a patient in need thereof. The composition comprises a pharmacologically acceptable lipoid as a hydrophilic phase, an effective amount of a photoreactive compound, a surfactant and a cosurfactant. The cosurfactant is a salt of a bile acid selected from the group of cholic acid, deoxycholic acid, glycocholic acid and mixtures thereof.

In addition, the present invention is concerned with a process for treating a patient with a poorly water soluble, pharmacologically active, photosensitizing compound which comprises administering to the patient the above defined emulsion. The treatment can be oxygen-dependent or oxygen-independent phototherapy and/or photodiagnosis.

The emulsions of the present invention can be fabricated employing excipients that are readily metabolizable and, as pure raw materials, are commercially available in pharmacologically acceptable forms at relatively modest cost. The compositions are both chemically and physically stable to terminal heat sterilization. Therefore, these emulsions are capable of being autoclaved. Furthermore, the compositions exhibit very good storage stability with no visible recrystallization of the drug. The emulsions are resistant to light in view of being relatively opaque.

These characteristics are quite different from those obtainable with prior art liposomal formulations. For example, liposomal formulations are not stable to heat and therefore cannot be sterilized employing heat. Instead, such require sterile filtration.

Liposomal formulations are not especially storage stable unless lyophilized. The liposomal formulations are very sensitive to light since the suspensions are translucent.

BEST AND VARIOUS MODES FOR CARRYING OUT INVENTION

Figure 1:
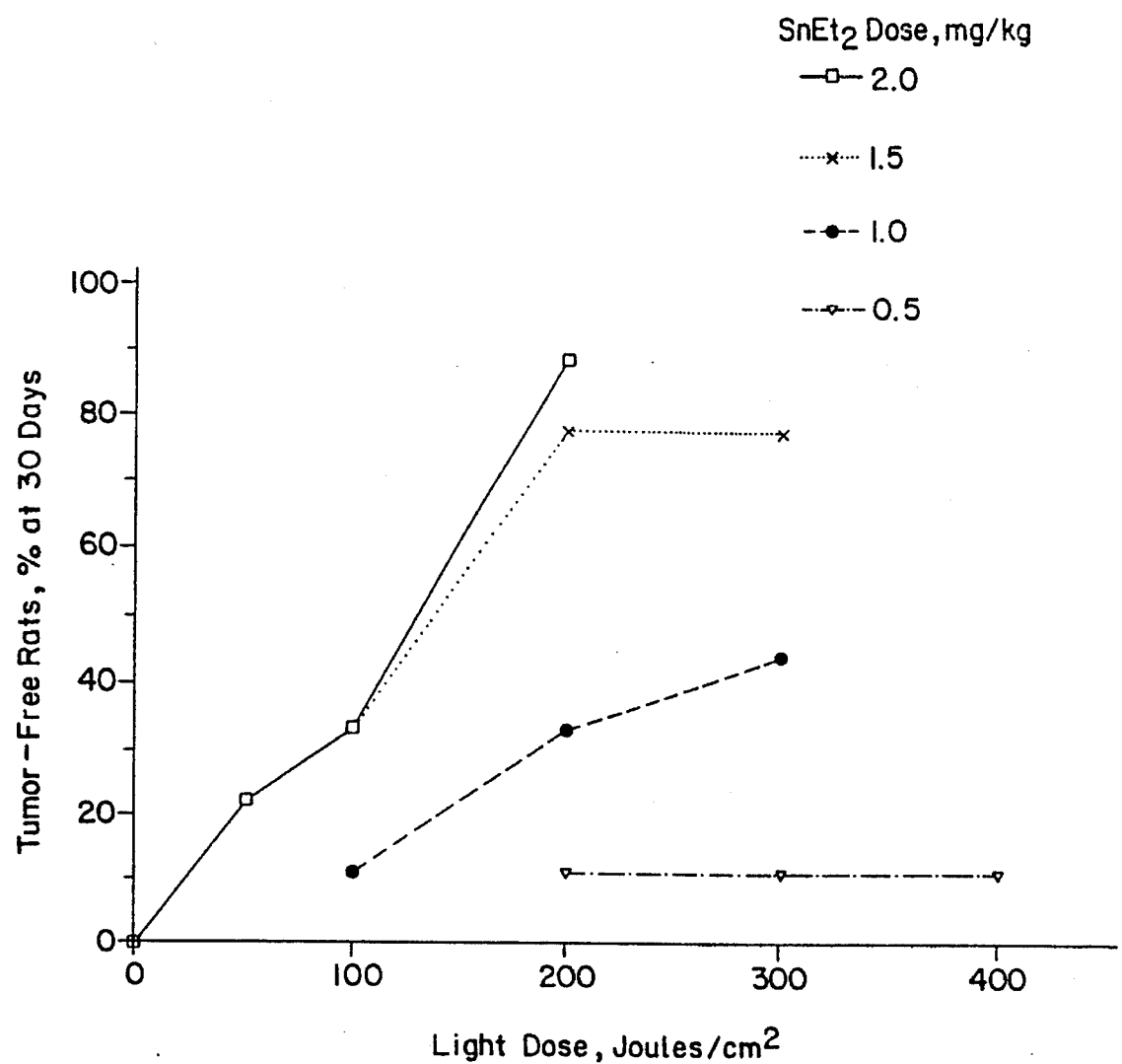
FIG. 1 illustrates tumor dose-response curves.

The photosensitizing compounds employed are poorly water soluble, photoreactive compounds and typically exhibit solubility in water of no greater than about 100 mg/liter. The preferred compounds of the present invention are the photoreactive pyrrole-derived macrocycles, including naturally occurring or synthetic porphyrins, naturally occurring or synthetic chlorins, naturally occurring or synthetic bacteriochlorins, synthetic isobacteriochlorins, phthalocyanines, naphthalocyanines, and expanded pyrrole-based macrocyclic systems such as porphycenes, sapphyrins, and texaphyrins, and derivatives thereof.

Examples of suitable pyrrole-based macrocyclic classes are illustrated by the following structural formulae:

Porphyrins:

Naturally Occurring:

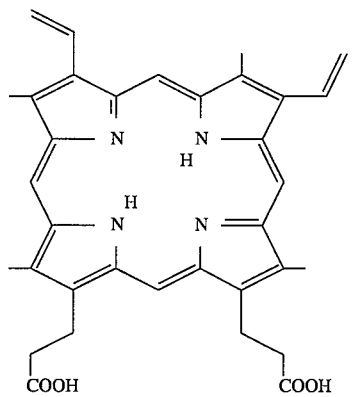

Protoporphyrin IX

Synthetic:

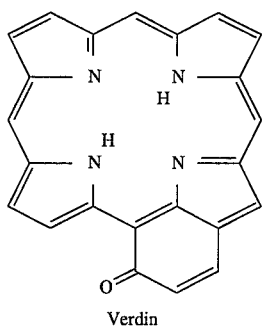

Verdin

Chlorins:

Naturally Occurring:

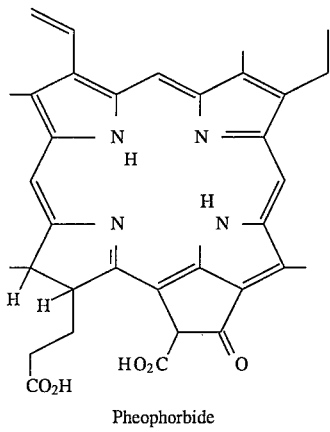

Pheophorbide

Synthetic:

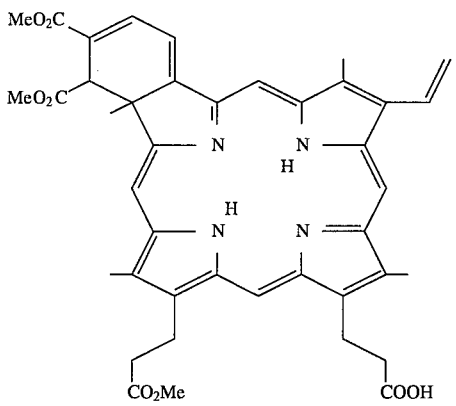

BPD mono acid ring A

Synthetic:
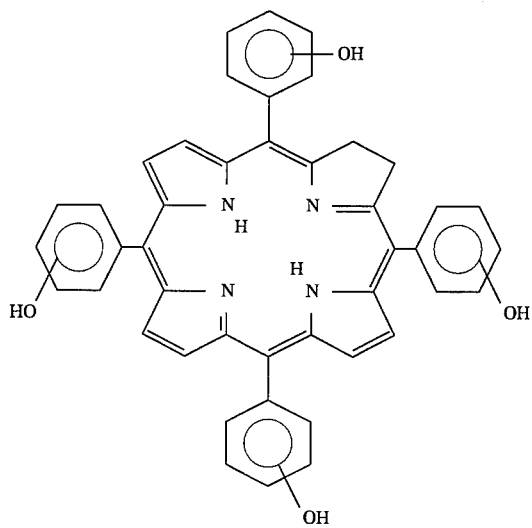
meso-tetra(hydroxyphenyl) Chlorin
Synthetic:
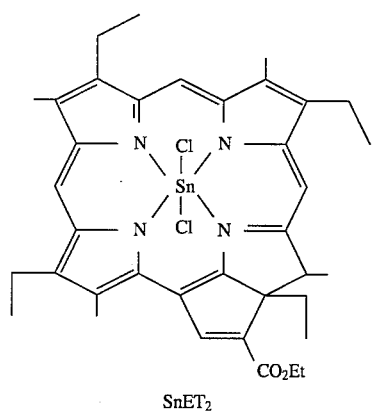
SnET$_2$
Bacteriochlorins:
Naturally Occurring:
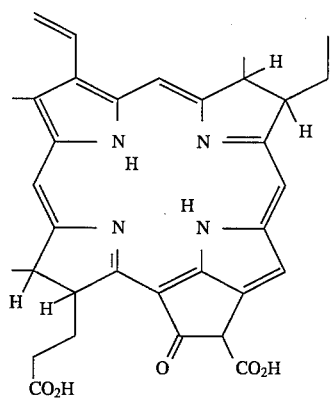
Bacteriopheophorbide
Synthetic:
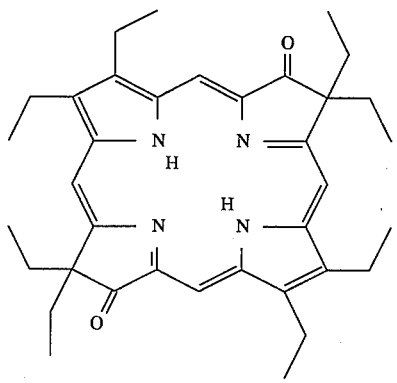
Octaethyldioxobacteriochlorin
Synthetic Isobacteriochlorin:
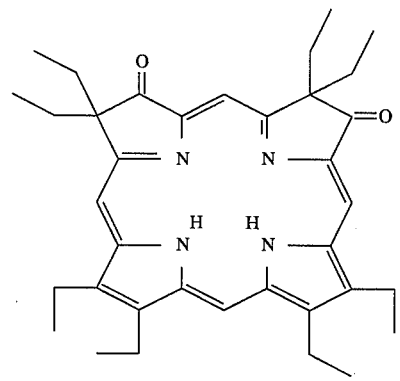
Octaethyldioxoisobacteriochlorin
Phthalocyanines:
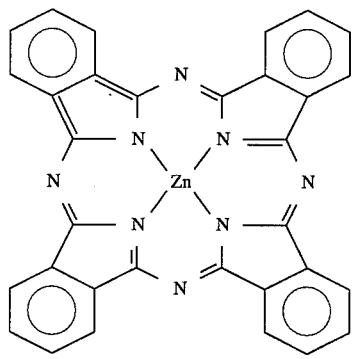
Zinc Phthalcyanine

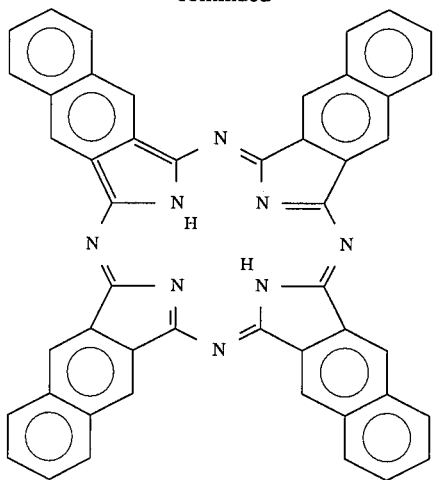

Naphthalocyanine

Porphycenes:

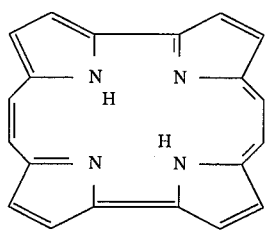

Sapphyrins:

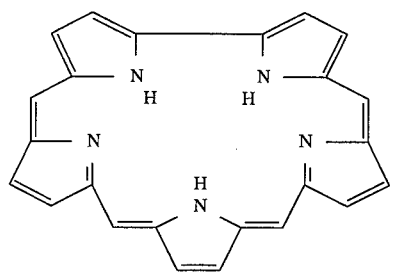

Texaphyrins:

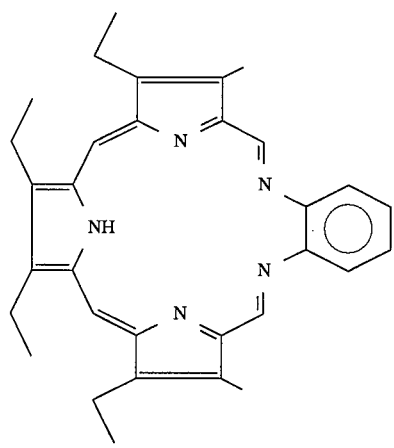

The pyrrole-derived macrocyclic compounds are typically employed in amounts of 0.01 to about 1 g/100 ml, preferably about 0.05 to about 0.5 gram/100 ml, typical of which being about 0.1g/100 ml.

The hydrophobic component comprises a pharmaceutically acceptable triglyceride, such as an oil or fat of a vegetable or animal nature, and preferably is selected from the group consisting of soybean oil, safflower oil, marine oil, black currant seed oil, borage oil, palm kernel oil, cotton seed oil, corn oil, sunflower seed oil, olive oil or coconut oil.

Physical mixtures of oils and/or interesterified mixtures can be employed, if desired.

The preferred oils are medium chain length triglycerides having $C_8$–$C_{10}$ chain length and more preferably being saturated. The preferred triglyceride is a distillate obtained from coconut oil.

The emulsions of the present invention usually have a fat or oil content of about 5 to about 50 g/100 ml, preferably about 10 to about 30 g/100 ml, a typical example being about 20 g/100 ml of the emulsion.

The emulsion of the present invention also contains a stabilizer such as phosphatides, soybean phospholipids, nonionic block copolymers of polyoxyethylene and polyoxypropylene (e.g. poloxamers), synthetic or semi-synthetic phospholipids, and the like. The preferred stabilizer is purified egg yolk phospholipid.

The stabilizer is usually present in the composition in amounts of about 0.1 to about 10, and preferably about 0.3 to about 3 grams/100 ml, a typical example being about 1.5 grams/100 ml.

Crucial to achieving the results desired by the present invention is the presence of certain bile acid salts as a costabilizer. The salts are pharmacologically acceptable salts of bile acids selected from the group of cholic acid, deoxycholic acid and glycocholic acid, and preferably of cholic acid. The salts are typically alkaline metal or alkaline earth metal salts and preferably sodium, potassium, calcium or magnesium salts, and most preferably, sodium salts. Mixtures of bile acid salts can be employed if desired.

The amount of bile acid salt employed is usually about 0.01 to about 1.0 and preferably about 0.05 to about 0.4 grams/100 ml, a typical example being about 0.2 grams/100 ml.

In addition, the emulsion should exhibit a pH of about 7.5 to about 9.5, and preferably about 8.5. The pH can be adjusted to the desired value, if necessary, by adding a pharmaceutically acceptable base, such as sodium hydroxide, potassium hydroxide, calcium hydroxide, magnesium hydroxide and ammonium hydroxide.

The emulsion also includes water for injection in the necessary amount to provide the desired volume.

If desired, the emulsion can include auxiliary ingredients, such as auxiliary surfactants, isotonic agents, antioxidants, nutritive agents, trace elements and vitamins.

The isotonic agents when employed are typically used in amounts of about 0.2 to about 8.0, preferably about 0.4 to about 4 grams/100 ml, an example of which being about 1.9 gram/100 ml. These materials regulate the osmotic pressure to make the emulsion isotonic with the blood.

Examples of some isotonic agents are glycerin, amino acids, such as alanine, histidine, glycine, and/or sugar alcohols, such as xylitol, sorbitol and/or mannitol.

Antioxidants can be used to enhance the stability of the emulsion, a typical example being α-tocopherol. When employed, such are used in amounts of about 0.005 to about 0.5, preferably about 0.02 to about 0.2 grams/100 ml, an example of which is about 0.1 grams/100 ml.

The emulsions can also contain auxiliary solvents, such as an alcohol, such as ethyl alcohol or benzyl alcohol, with ethyl alcohol being preferred. When employed, such is typically present in amounts of about 0.1 to about 4.0, and preferably about 0.2 to about 2 grams/100 ml, a typical example being about 1 gram/100 ml.

The ethanol is advantageous since it facilitates dissolution of the poorly water-soluble photosensitizing compound, and especially those that form crystals which may be very difficult to dissolve in the oil phase. Accordingly, the ethanol must be added directly to the oil phase during preparation to be effective. For maximum effectiveness, the ethanol should constitute about 5% to 15% by weight of the oil phase. In particular, if ethanol constitutes less than 5% by weight of the oil phase, dissolution of the photosensitizing compound becomes unacceptably slow. If the ethanol concentration exceeds 15%, then the final concentration in finished product is too high, and emulsion quality deteriorates significantly. Higher ethanol levels promote the formation of large, poorly emulsified oil droplets (>5 µm diameter) which are unacceptable in an injectable product.

The emulsions of the present invention can be administered by those techniques known in the art, including orally and parenterally, such as intravenously, intramuscularly and subcutaneously. When administered or introduced into the blood vessels, the particles in the emulsion are less than about 5 µm in diameter, and most preferably about 0.5 µm or below.

The emulsions of the present invention satisfy the need for a stable, pharmacologically-suitable, lipid-based delivery system, while at the same time meeting the specific requirements for retaining drug efficacy in vivo. The vehicle composition employed in the present invention is suitable for injection since, among other things, it avoids pharmaceutically undesirable organic solvents, solubilizers, oils or emulsifiers.

The oil-in-water emulsions of the present invention are prepared along the following lines. The triglyceride oil is heated to 50°–70° C. while sparging with nitrogen gas. The required amounts of stabilizer (e.g. egg yolk phospholipids), bile acid salt, alcohol (e.g. ethanol), antioxidant (e.g. α-tocopherol) and photosensitizing compound are added to the triglyceride while processing for about 5 to about 20 mlnutes with a high speed blender or overhead mixer to ensure complete dissolution or uniform suspension.

In a separate vessel, the required amounts of water and isotonic agent (e.g. -glycerin) are heated to the above temperature (e.g. 50°–70°) while sparging with nitrogen gas.

Next, the aqueous phase is transferred into the prepared oil phase and high speed blending is continued for another 5 to 10 mlnutes to produce a uniform but coarse preemulsion (or premix). This premix is then transferred to a conventional high pressure homogenizer (APV Gaulin) for emulsification at about 8,000–10,000 psi. The diameter of the dispersed oil droplets in the finished emulsion will be less than 5 µm, with a large proportion less than 1 µm. The mean diameter of these oil droplets will be less than 1 µm, preferably from 0.2 to 0.5 µm. The emulsion product is then filled into borosilicate (Type 1) glass vials which are stoppered, capped and terminally heat sterilized in a rotating steam autoclave at about 121° C.

The emulsions of the present invention are capable of withstanding autoclaving as well as freezing at about 0° to −20° C. Such can be stored for a relatively long time with minimal physical and chemical breakdown, i.e. at least 12–18 months at 4°–8° C.

The vehicle composition employed in the present invention is chemically inert with respect to the incorporated pharmacologically active photosensitizing compound.

The emulsions of the present invention exhibit very low toxicity following intravenous administration and exhibit no venous irritation and no pain on injection. The emulsions exhibit minimal physical and chemical changes (e.g. formation of non-emulsified surface oil) during controlled shake-testing on a horizontal platform. Moreover, the oil-in-water emulsions of the present invention promote desirable pharmacoldnetics and tissue distribution of the photoreactive drug in vivo.

The following non-limiting examples are presented to further illustrate the present invention.

In particular, the following illustrates a unique interactive nature of the excipients in the present invention, which results in an enhanced drug solubility. By way of example, it was possible to solubilize only about 0.4 mg of tin ethyl etiopurpurin (SnEt$_2$) per gram of oil. Therefore, a 20% w/v oil-in-water emulsion would contain only 0.4/5 =0.08 mg/ml of drug. Such a low concentration would severely limit clinical utility by requiring large injection volumes with unacceptably high fat loads. However, the present invention successfully delivers over ten times this concentration of SnEt$_2$.

Tin ethyl etiopurpurin:

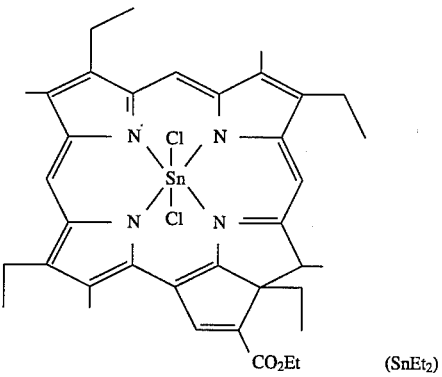

(SnEt$_2$)

EXAMPLE 1

In 5 ml glass tubes, medium chain length oil also known as MCT oil (Miglyol 810, Hüls America, Piscataway, N.J.) is combined with 10 mg/gm SnEt$_2$ plus excipients, shown in Table I. When used, excipients are added at the following concentrations (mg/gm oil): ethanol, 50; egg phospholipids, 75; and sodium cholate, 10. After incubating for 30 minutes at 55° C., the tubes stand overnight at room temperature (19°–22° C). The tubes are centrifuged to remove bulk precipitates, and supernatants are filtered through 0.45 µm nylon membrane to remove any undissolved drug. Aliquots of filtrate are then diluted in chloroform:isopropyl alcohol (1:1) for spectrophotometric determination of drug concentration (absorbance at 662 nm). Reference standards are prepared with known concentrations of SnEt$_2$ in the same solvent.

TABLE I

Drug Solubility in Oil

| Excipient Combination Added to MCT Oil | SnEt$_2$ Concentration mg/gm oil | SnEt$_2$ Concentration Normalized |
|---|---|---|
| MCT oil alone | 0.38 | 1.00 |
| + ethanol | 0.28 | 0.74 |
| + egg phospholipids (EYP) | 0.89 | 2.34 |
| + Na cholate | 1.17 | 3.08 |
| + ethanol + EYP | 1.37 | 3.61 |
| + EYP + Na cholate | 1.77 | 4.66 |
| + ethanol + Na cholate | 2.20 | 5.79 |
| + ethanol + EYP + Na cholate | 4.92 | 12.95 |

EXAMPLE 2

This example illustrates relative efficiencies of several bile salts. Mixtures of MCT oil, egg phospholipids, ethanol, and SnEt$_2$ were incubated with different bile salts, all at 4.6 mM[1], under the same conditions described above in Example 1. As shown in Table II below, sodium cholate is the most efficient solubilizer. Cholic acid lacks solubilizing action in the oil.

TABLE II

Sodium Cholate is the Most Efficient Co-Solubilizer for SnEt$_2$

| Bile compound | SnEt$_2$ Concentration mg/gm Oil | SnEt$_2$ Concentration Normalized |
|---|---|---|
| None | 1.26 | 1.00 |
| Na tauracholate | 1.13 | 0.90 |
| Cholic acid | 1.33 | 1.06 |
| Na glycocholate | 2.22 | 1.76 |
| Na deoxycholate | 2.31 | 1.83 |
| Na cholate | 3.70 | 2.94 |

[1] equivalent to sodium cholate addition at 10 mg per gram oil or 0.2% w/v in a 20% o/w emulsion

[1] equivalent to sodium cholate addition at 10 mg per gram oil or 0.2% w/v in a 20% o/w emulsion

EXAMPLE 3

This example illustrates the cosurfactant activity exhibited by the bile acid salt. In particular, net electronegative charge (Zeta potential) on the emulsified oil droplets is measured by changes in electrophoretic mobility at pH 8.0 (Malvern Zetasizer 2c). Since the pKa for cholic acid is 6.4, full ionization is expected at the alkaline pH of the emulsions. Despite high expected solubility in water (>569 g/l at 15° C), cholate anion appears to associate with phospholipids on the droplet surface. By doing so, cholate increases the Zeta potential of phospholipid-stabilized emulsions, as shown in Table III. The result is an enhanced physical stability for this invention, as measured by a standardized platform shake test. A relationship between Zeta potential and physical stability of colloidal systems has been documented.

TABLE III

Sodium Cholate Increases Electronegative Zeta for Emulsions

| Sample | Zeta Potential (−mV) in Diluent at pH 8.0[2] | |
|---|---|---|
|  | 5.0 mM Hepes | 4.6 mM Na Cholate |
| Standard latex beads[3] | −37.2 ± 0.5 | −38.7 ± 0.3 |
| Intralipid 20% ® | −36.4 ± 0.3 | −58.2 ± 1.0 |
| TEP emulsion | −30.2 ± 1.1 | −52.5 ± 0.2 |

[2] Hepes or cholate added directly to emulsion and to diluent prior to Zeta measurements
[3] IDS Spheres, Portland, OR; Cat. No. 10-36-23, 0.865 μm The SnEt$_2$ emulsion is prepared in the manner discussed above using the formulation described in Table IV:

TABLE IV

SnEt$_2$ Emulsion Formulation

| INGREDIENT | GRAMS/100 ml |
|---|---|
| medium chain triglycerides (Miglyol 810) | 20.0 |
| egg yolk phospholipids | 1.5 |
| sodium cholate | 0.2 |
| ethanol, USP | 1.0 |
| dl α-tocopherol, USP | 0.1 |
| tin ethyl etiopurpurin | 0.1 |
| glycerin, USP | 1.9 |
| sodium hydroxide, USP [pH adjustment] | 7.5–9.5 |
| water for injection, USP | q.s. |

EXAMPLE 4

Fischer 344 rats, engrafted with transplantable, chemically-induced (FANFT) urothelial tumors, were treated with tin ethyl etiopurpurin (SnEt$_2$) and red light (660 nm). SnEt$_2$ was administered as a bolus injection via lateral tail vein, using the emulsion described by the present invention. Tumor response was assessed in groups of nine animals injected with one of four doses of drug and exposed to one of three different doses of light, as summarized in FIG. 1. Control animals received emulsion vehicle without drug. Animals were monitored for tumor re-growth, tissue changes at treatment site, and general health three times per week for a period of 30 days after light treatment.

By determining the number of tumor-free rats 30 days after each treatment, tumor dose-response curves for drug and light were generated, shown in FIG. 1.

When administered in the emulsion delivery system described by the present invention, SnEt$_2$ and red laser light were effective in the treatment of transplantable, FANFT-induced, urothelial tumors in the fisher 344 rat. A dose and light response by the tumor was demonstrated. No adverse clinical events were observed and no deaths occurred which could be attributed to the drug-emulsion treatment. Current protocols for human clinical trials make use of the present invention with SnEt$_2$ as the photosensitizing drug.

What is claimed is:

1. An emulsion for administering a poorly water-soluble, pharmacologically active, photosensitizing pyrrole-based macrocyclic compound to a patient comprising a pharmacologically acceptable lipid as a hydrophobic phase dispersed in a hydrophilic phase, an effective amount of said photosensitizing pyrrole-based macrocyclic compound, a phospholipids stabilizer, and as a costabilizer, a pharmaceutically acceptable salt of a bile acid selected from the group consisting of cholic acid, deoxycholic acid, glycocholic acid; and mixtures thereof, and wherein the concentration of said pharmaceutically acceptable salt is about 0.01 to about 1.0 g/100 ml of the emulsion.

2. The emulsion of claim 1 wherein said lipoid is selected from the group consisting of soybean oil, safflower oil, marine oil, black currant seed oil, borage oil, palm kernel oil, sunflower oil, cotton seed oil, olive oil, coconut oil and physical or interesterified mixtures thereof.

3. The emulsion of claim 1 wherein said lipoid is a triglyceride having a fatty acid chain length of 8 to 10 carbons.

4. The emulsion of claim 1 wherein said lipoid is the triglycerides distilled from coconut oil.

5. The emulsion of claim 1 wherein said stabilizer is egg yolk phospholipids.

6. The emulsion of claim 1 wherein the particles have a mean diameter of less than 5 mlcrons.

7. The emulsion of claim 1 wherein said diameter is 0.5 mlcrons or less.

8. The emulsion of claim 1 wherein the amount of said photosensitizing compound is about 0.01 to about 1 g/100 ml, the amount of said lipoid is about 5 to about 40 g/100 ml, and the amount of said salt of a bile acid is about 0.05 to about 0.4 g/100 ml.

9. The emulsion of claim 1 wherein the amount of said stabilizer is about 0.3 to about 3 g/100 ml.

10. The emulsion of claim 1 which further includes an isotonic agent.

11. The emulsion of claim 10 wherein said isotonic agent is present in an amount of about 0.4 to about 4 g/100 ml.

12. The emulsion of claim 10 wherein said isotonic agent is glycerin.

13. The emulsion of claim 1 which further includes an antioxidant.

14. The emulsion of claim 13 wherein the antioxidant is present in an amount of about 0.02 to about 0.2 g/100 ml.

15. The emulsion of claim 14 wherein said antioxidant is α-tocopherol.

16. The emulsion of claim 1 wherein said salt of a bile acid is a salt of cholic acid.

17. The emulsion of claim 16 wherein said salt is sodium cholate.

18. The emulsion of claim 1 which further includes ethyl alcohol.

19. The emulsion of claim 18 wherein the amount of said ethyl alcohol is about 0.2 to about 2 grams/100 ml.

20. The emulsion of claim 1 wherein said pyrrolic macrocyclic compound is selected from the group consisting of at least one of naturally occurring or synthetic porphyrins, naturally occurring or synthetic chlorins, naturally occurring or synthetic bacteriochlorins, synthetic isobacteriochlorins, phthalocyanines, naphthalocyanines, and expanded pyrrole-based macrocyclic systems.

21. The emulsion of claim 20 wherein said pyrrolic macrocyclic compound is tin ethyl etiopurpurin.

22. The emulsion of claim 20 wherein said pyrrolic macrocyclic compound is zinc phthalocyanine.

23. The emulsion of claim 20 wherein said pyrrolic macrocyclic compound is benzoporphyrin derivative.

24. The emulsion of claim 20 wherein said pyrrolic macrocyclic compound is meso-tetra (hydroxyphenyl) chlorin.

25. A method for treating a patient with a photosensitizing compound which comprises administering to said patient the emulsion of claim 1.

26. The method of claim 25 wherein said administering is intravenously.

27. The method of claim 25 which further comprises exposing said pyrrolic macrocyclic compound to light after administering in order to activate said compound.

28. A method for diagnosing a patient for tumors which comprises administering to said patient the emulsion of claim 1 and then exposing said patient to light of a suitable wavelength that would induce fluorescence of any photosensitizing compound preferentially maintained by hyperproliferating or abnormal cells in said patient.

29. The emulsion of claim 1 having a pH of about 7.5 to about 9.5.

30. The emulsion of claim 20 wherein said expanded pyrrole-base macrocyclic systems is selected from the group consisting of porphycenes, sapphyrins and texaphyrins.

31. The emulsion of claim 1 wherein said stabilizer consists of phospholipids in an amount of about 0.3 to about 3 g/100 ml of said emulsion and said costabilizer consists of said salt of a bile acid in an amount of about 0.05 to about 0.4 g/100 ml.

* * * * *

UNITED STATES PATENT AND TRADEMARK OFFICE
CERTIFICATE OF CORRECTION

PATENT NO. :   5,616,342
DATED        :   April 1, 1997
INVENTOR(S): Lyons

It is certified that error appears in the above-identified patent and that said Letters Patent is hereby corrected as shown below:

On the title page, item [54] and Col. 1, lines 1-4,
The title of the invention should read:

Emulsion Suitable for Administering a Poorly Water-Soluble Photosensitizing Compound and Use Thereof Signed and Sealed this Fourteenth Day of October, 1997

Attest:

Attesting Officer

BRUCE LEHMAN

Commissioner of Patents and Trademarks